(12) United States Patent
Ogasawara

(10) Patent No.: US 7,456,567 B2
(45) Date of Patent: Nov. 25, 2008

(54) ORGANIC ELECTROLUMINESCENT DEVICE, AND AZEPINE COMPOUND AND METHOD FOR PRODUCING THE SAME

(75) Inventor: Jun Ogasawara, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 341 days.

(21) Appl. No.: 11/223,038

(22) Filed: Sep. 12, 2005

(65) Prior Publication Data

US 2007/0232800 A1 Oct. 4, 2007

(30) Foreign Application Priority Data

Sep. 14, 2004 (JP) .............................. 2004-267535

(51) Int. Cl.
 *H01L 51/00* (2006.01)
 *C07D 223/14* (2006.01)
 *C07D 487/00* (2006.01)
 *C07D 487/14* (2006.01)
 *C07D 491/00* (2006.01)

(52) U.S. Cl. ........................... 313/504; 257/40; 257/51; 540/576; 540/577

(58) Field of Classification Search ........................ None
See application file for complete search history.

(56) References Cited

FOREIGN PATENT DOCUMENTS

| JP | 10-59943 A | 3/1998 |
|---|---|---|
| JP | 2001-97953 A | 4/2001 |

*Primary Examiner*—James Wilson
*Assistant Examiner*—Noble Jarrell
(74) *Attorney, Agent, or Firm*—Birch, Stewart, Kolasch & Birch, LLP

(57) ABSTRACT

An organic electroluminescent device having a pair of electrodes, and at least one organic layer interposed between the pair of electrodes, with the organic layer containing at least one compound represented by formula (1):

Formula (1)

$$\begin{array}{c} L^{11}-N-L^{13} \\ | \quad | \quad | \\ L^{12}-L^{15}-L^{14} \end{array}$$

wherein $L^{11}$, $L^{13}$, and $L^{14}$ each independently represent an o-arylene group, an o-heteroarylene group, or a vinylene group; $L^{12}$ represents an o-arylene group, an o-heteroarylene group, a vinylene group, or an ethylene group; and $L^{15}$ represents a trivalent or higher aromatic ring or a trivalent or higher aromatic heterocyclic ring; and a compound represented by formula (2):

Formula (2)

wherein $L^{21}$, $L^{22}$, $L^{23}$, $L^{24}$, and $L^{25}$ each independently represent a group necessary for forming an aromatic ring or a group necessary for forming an aromatic heterocyclic ring; and a method for producing a compound represented by formula (2).

5 Claims, 1 Drawing Sheet

ORGANIC ELECTROLUMINESCENT DEVICE, AND AZEPINE COMPOUND AND METHOD FOR PRODUCING THE SAME

FIELD OF THE INVENTION

The present invention relates to an organic electroluminescent device capable of converting electric energy to light, to emit light, and an azepine compound and a method for producing thereof.

BACKGROUND OF THE INVENTION

Today active research and development are carried out on various display devices. Of the devices, organic electroluminescence (EL) devices (hereinafter, referred to as EL devices, or luminescent devices) can give luminescence having high brightness at low voltage, and therefore attention is paid to the devices as promising display devices.

JP-A-10-59943 ("JP-A" means unexamined published Japanese patent application) discloses a compound having an azepine structure, which is employable in an organic electroluminescent device. However, the structures disclosed are severely limited.

Generally, further, a compound having an azepine structure requires multi-steps for a method of synthesis thereof. JP-A-2001-97953 discloses a synthesis method using no special reagent, and although this method is to derive a compound having an azepine structure from commercially available materials, it requires a multi-step process. As such, there has been demanded for a method of synthesizing a compound having an azepine structure by fewer steps.

SUMMARY OF THE INVENTION

The present invention resides in an organic electroluminescent device that includes a pair of electrodes, and at least one organic layer interposed between the pair of electrodes, with the organic layer containing at least one compound represented by formula (1):

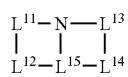

Formula (1)

wherein $L^{11}$, $L^{13}$, and $L^{14}$ each independently represent an o-arylene group, an o-heteroarylene group, or a vinylene group; $L^{12}$ represents an o-arylene group, an o-heteroarylene group, a vinylene group, or an ethylene group; and $L^{15}$ represents a trivalent or higher aromatic ring or a trivalent or higher aromatic heterocyclic ring.

Further, the present invention resides in a compound represented by formula (2):

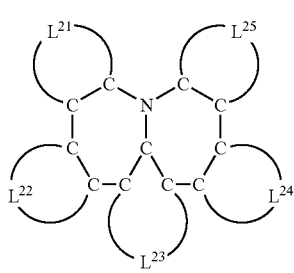

Formula (2)

wherein $L^{21}$, $L^{22}$, $L^{23}$, $L^{24}$, and $L^{25}$ each independently represent a group necessary for forming an aromatic ring or a group necessary for forming an aromatic heterocyclic ring.

Further, the present invention resides in a method for producing a compound represented by formula (5), which comprises reacting a compound represented by formula (3) with a compound represented by formula (4):

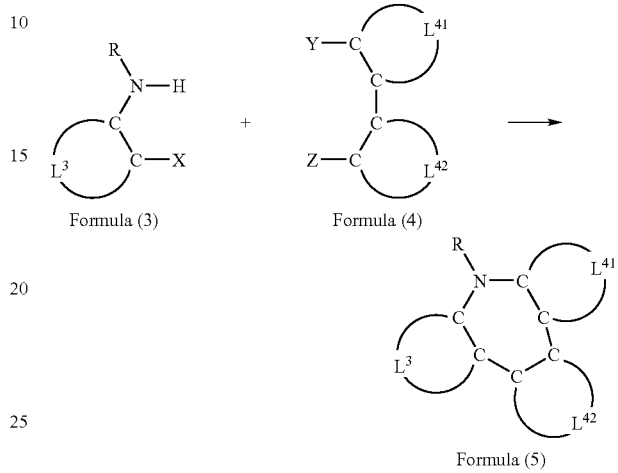

wherein $L^3$, $L^{41}$, and $L^{42}$ each independently represent a group necessary for forming an aromatic ring or a group necessary for forming an aromatic heterocyclic ring; X, Y, and Z each independently represent a hydrogen atom or a group that splits off in the reaction, and at least one of Y and Z is the group that splits off in the reaction; and R represents a hydrogen atom or a substituent.

Further, the present invention resides in a method for producing a compound represented by formula (2), which comprises reacting a compound represented by formula (3a) with a compound represented by formula (4a):

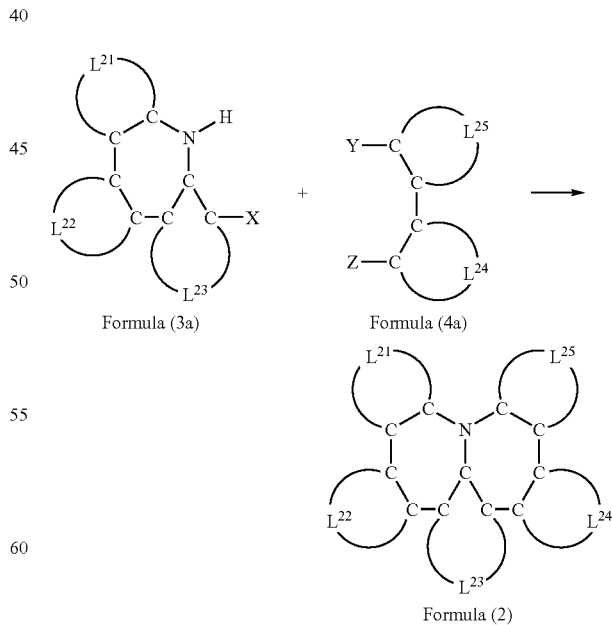

wherein $L^{21}$, $L^{22}$, $L^{23}$, $L^{24}$, and $L^{25}$ each independently represent a group necessary for forming an aromatic ring or a group necessary for forming an aromatic heterocyclic ring; X, Y, and Z each independently represent a hydrogen atom or a group that splits off in the reaction, and at least one of Y and Z is the group that splits off in the reaction.

Other and further features and advantages of the invention will appear more fully from the following description, taken in connection with the accompanying drawing.

DETAILED DESCRIPTION OF THE INVENTION

Figure 1:
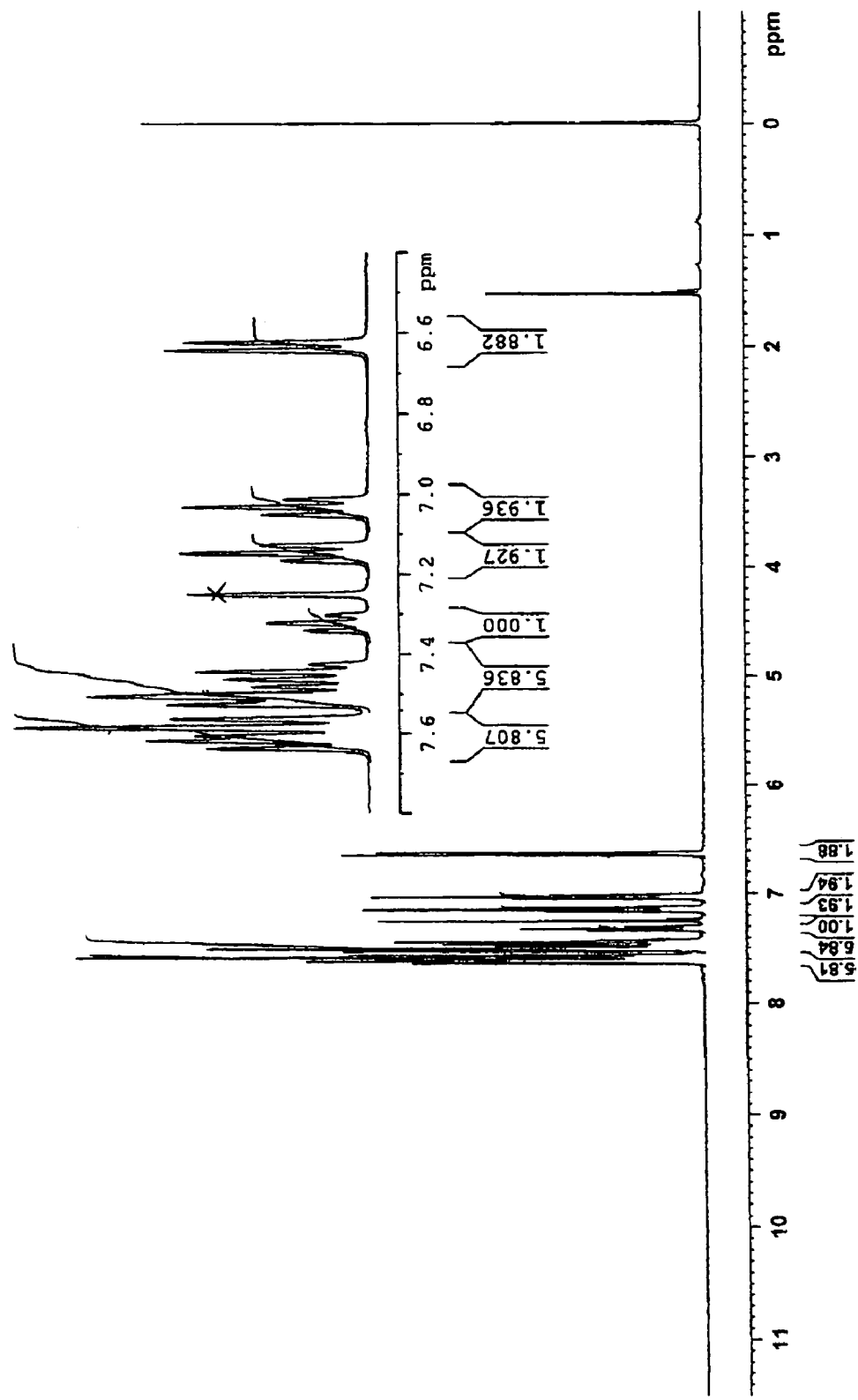
FIG. 1 is a drawing showing NMR spectrum of Compound (1-1) obtained in Example 2.

According to the present invention, there is provided the following means:

(1) An organic electroluminescent device having a pair of electrodes, and at least one organic layer interposed between the pair of electrodes, with the organic layer containing at least one compound represented by formula (1):

Formula (1)

wherein $L^{11}$, $L^{13}$, and $L^{14}$ each independently represent an o-arylene group, an o-heteroarylene group, or a vinylene group; $L^{12}$ represents an o-arylene group, an o-heteroarylene group, a vinylene group, or an ethylene group; and $L^{15}$ represents a trivalent or higher aromatic ring or a trivalent or higher aromatic heterocyclic ring.

(2) The organic electroluminescent device as recited in (1), wherein the compound represented by formula (1) is a compound represented by formula (2):

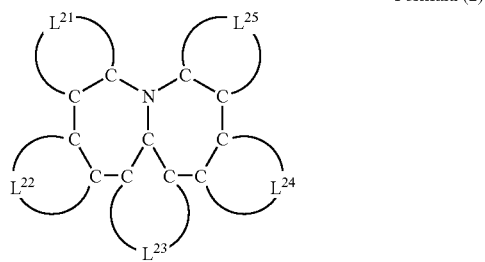

Formula (2)

wherein $L^{21}$, $L^{22}$, $L^{23}$, $L^{24}$, and $L^{25}$ each independently represent a group necessary for forming an aromatic ring or a group necessary for forming an aromatic heterocyclic ring.

(3) A compound represented by formula (2):

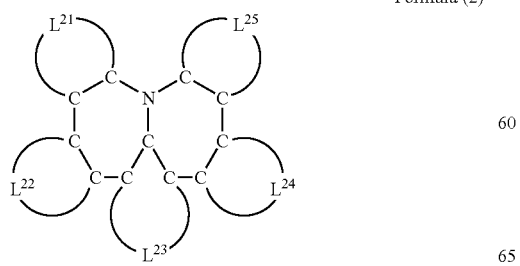

Formula (2)

wherein $L^{21}$, $L^{22}$, $L^{23}$, $L^{24}$, and $L^{25}$ each independently represent a group necessary for forming an aromatic ring or a group necessary for forming an aromatic heterocyclic ring.

(4) A method for producing a compound represented by formula (5), which comprises reacting a compound represented by formula (3) with a compound represented by formula (4):

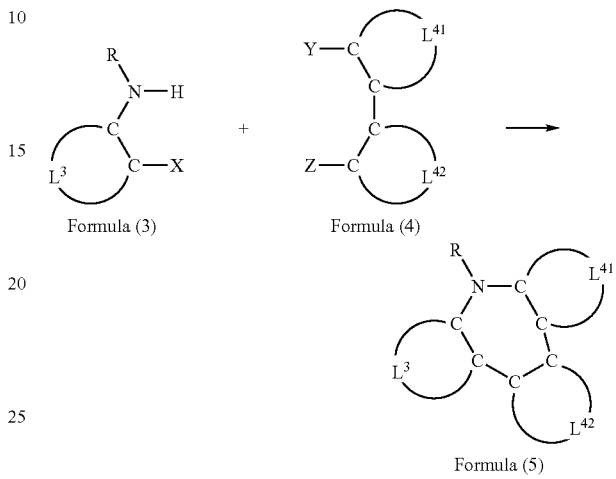

wherein $L^3$, $L^{41}$, and $L^{42}$ each independently represent a group necessary for forming an aromatic ring or a group necessary for forming an aromatic heterocyclic ring; X, Y, and Z each independently represent a hydrogen atom or a group that splits off in the reaction, and at least one of Y and Z is the group that splits off in the reaction; and R represents a hydrogen atom or a substituent.

(5) A method for producing a compound represented by formula (2), which comprises reacting a compound represented by formula (3a) with a compound represented by formula (4a):

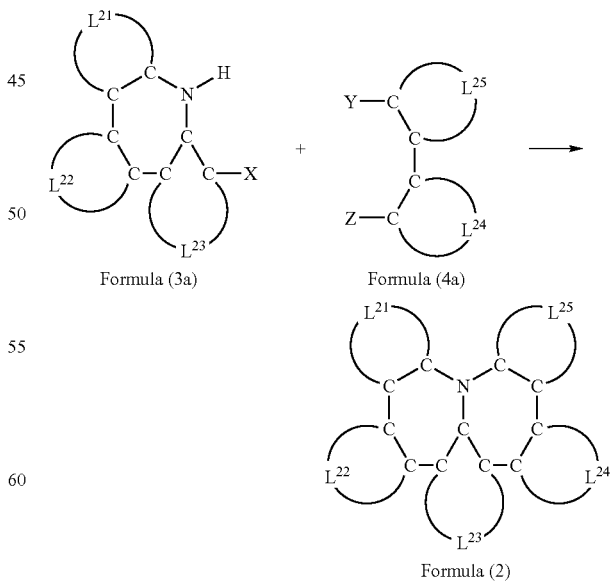

wherein $L^{21}$, $L^{22}$, $L^{23}$, $L^{24}$, and $L^{25}$ each independently represent a group necessary for forming an aromatic ring or a group necessary for forming an aromatic heterocyclic ring; X, Y, and Z each independently represent a hydrogen atom or a group that splits off in the reaction, and at least one of Y and Z is the group that splits off in the reaction.

The present invention will be explained in detail hereinafter.

An embodiment of the present invention is an organic electroluminescent device having a pair of electrodes and at least one organic layer (which comprises at least one light-emitting layer) interposed between the pair of electrodes, with the organic layer containing at least one compound represented by formula (1).

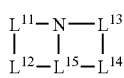

Formula (1)

wherein $L^{11}$, $L^{13}$, and $L^{14}$ each independently represent an o-arylene group, an o-heteroarylene group, or a vinylene group; $L^{12}$ represents an o-arylene group, an o-heteroarylene group, a vinylene group, or an ethylene group; and $L^{15}$ is a trivalent or higher aromatic ring or a trivalent or higher aromatic heterocyclic ring.

The compounds represented by formula (1) will be explained in detail.

Each of $L^{11}$, $L^{13}$, and $L^{14}$ represents independently an o-arylene group, an o-heteroarylene group, or a vinylene group.

Each of $L^{11}$, $L^{13}$, and $L^{14}$ represents preferably an o-arylene group, more preferably an o-phenylene group, a 2,3-naphthylene group, or a 2,3-anthrylene group, and still more preferably an o-phenylene group.

Each of $L^{11}$, $L^{13}$, and $L^{14}$ may have a substituent. Examples of the substituent that each of $L^{11}$, $L^{13}$, and $L^{14}$ may have include substituents listed in the following Group A substituents.

(Group A Substituents)

Examples of the Group A substituents include an alkyl group (preferably an alkyl group having 1 to 30 carbon atoms, more preferably 1 to 20 carbon atoms, and most preferably 1 to 10 carbon atoms, e.g., methyl, ethyl, iso-propyl, tert-butyl, n-octyl, n-decyl, n-hexadecyl, cyclopropyl, cyclopentyl, cyclohexyl), an alkenyl group (preferably an alkenyl group having 2 to 30 carbon atoms, more preferably 2 to 20 carbon atoms, and most preferably 2 to 10 carbon atoms, e.g., vinyl, allyl, 2-butenyl, 3-pentenyl), an alkynyl group (preferably an alkynyl group having 2 to 30 carbon atoms, more preferably 2 to 20 carbon atoms, and most preferably 2 to 10 carbon atoms, e.g., propargyl, 3-pentynyl), an aryl group (preferably an aryl group having 6 to 30 carbon atoms, more preferably 6 to 20 carbon atoms, and most preferably 6 to 12 carbon atoms, e.g., phenyl, p-methylphenyl, naphthyl, anthranyl), an amino group (preferably an amino group having 0 to 30 carbon atoms, more preferably 0 to 20 carbon atoms, most preferably 0 to 10 carbon atoms, e.g., amino, methylamino, dimethylamino, diethylamino, dibenzylamino, diphenylamino, ditolylamino), an alkoxy group (preferably an alkoxy group having 1 to 30 carbon atoms, more preferably 1 to 20 carbon atoms, most preferably 1 to 10 carbon atoms, e.g., methoxy, ethoxy, butoxy, 2-ethylhexyloxy), an aryloxy group (preferably an aryloxy group having 6 to 30 carbon atoms, more preferably 6 to 20 carbon atoms, most preferably 6 to 12 carbon atoms, e.g., phenyloxy, 1-naphthyloxy, 2-naphthyloxy), a heteroaryloxy group (a heteroaryloxy group having preferably 1 to 30 carbon atoms, more preferably 1 to 20 carbon atoms, most preferably 1 to 12 carbon atoms, e.g., pyridyloxy, pyrazyloxy, pyrimidyloxy, quinolyloxy), an acyl group (preferably an acyl group having 1 to 30 carbon atoms, more preferably 1 to 20 carbon atoms, most preferably 1 to 12 carbon atoms, e.g., acetyl, benzoyl, formyl, pivaloyl), an alkoxycarbonyl group (preferably an alkoxycarbonyl group having 2 to 30 carbon atoms, more preferably 2 to 20 carbon atoms, most preferably 2 to 12 carbon atoms, e.g., methoxycarbonyl, ethoxycarbonyl), an aryloxycarbonyl group (preferably an aryloxycarbonyl group having 7 to 30 carbon atoms, more preferably 7 to 20 carbon atoms, most preferably 7 to 12 carbon atoms, e.g., phenyloxycarbonyl), an acyloxy group (preferably an acyloxy group having 2 to 30 carbon atoms, more preferably 2 to 20 carbon atoms, and most preferably 2 to 10 carbon atoms, e.g., acetoxy, benzoyloxy), an acylamino group (preferably an acylamino group having 2 to 30 carbon atoms, more preferably 2 to 20 carbon atoms, and most preferably 2 to 10 carbon atoms, e.g., acetylamino, benzoylamino), an alkoxycarbonylamino group (preferably an alkoxycarbonylamino group having 2 to 30 carbon atoms, more preferably 2 to 20 carbon atoms, and most preferably 2 to 12 carbon atoms, e.g., methoxycarbonylamino), an aryloxycarbonylamino group (preferably an aryloxycarbonylamino group having 7 to 30 carbon atoms, more preferably 7 to 20 carbon atoms, and most preferably 7 to 12 carbon atoms, e.g., phenyloxycarbonylamino), a sulfonylamino group (preferably a sulfonylamino group having 1 to 30 carbon atoms, more preferably 1 to 20 carbon atoms, and most preferably 1 to 12 carbon atoms, e.g., methanesulfonylamino, benzenesulfonylamino), a sulfamoyl group (preferably a sulfamoyl group having 0 to 30 carbon atoms, more preferably 0 to 20 carbon atoms, and most preferably 0 to 12 carbon atoms, e.g., sulfamoyl, methylsulfamoyl, dimethylsulfamoyl, phenylsulfamoyl), a carbamoyl group (preferably a carbamoyl group having 1 to 30 carbon atoms, more preferably 1 to 20 carbon atoms, and most preferably 1 to 12 carbon atoms, e.g., carbamoyl, methylcarbamoyl, diethylcarbamoyl, phenylcarbamoyl), an alkylthio group (preferably an alkylthio group having 1 to 30 carbon atoms, more preferably 1 to 20 carbon atoms, and most preferably 1 to 12 carbon atoms, e.g., methylthio, ethylthio), an arylthio group (preferably an arylthio group having 6 to 30 carbon atoms, more preferably 6 to 20 carbon atoms, and most preferably 6 to 12 carbon atoms, e.g., phenylthio), a heteroarylthio group (preferably a heteroarylthio group having 1 to 30 carbon atoms, more preferably 1 to 20 carbon atoms, most preferably 1 to 12 carbon atoms, e.g., pyridylthio, 2-benzimidazolylthio, 2-benzoxazolylthio, 2-benzothiazolylthio), a sulfonyl group (preferably a sulfonyl group having 1 to 30 carbon atoms, more preferably 1 to 20 carbon atoms, and most preferably 1 to 12 carbon atoms, e.g., mesyl, tosyl), a sulfinyl group (preferably a sulfinyl group having 1 to 30 carbon atoms, more preferably 1 to 20 carbon atoms, and most preferably 1 to 12 carbon atoms, e.g., methanesulfinyl, benzenesulfinyl), a ureido group (preferably a ureido group having 1 to 30 carbon atoms, more preferably 1 to 20 carbon atoms, and most preferably 1 to 12 carbon atoms, e.g., ureido, methylureido, phenylureido), a phosphoric acid amido group (preferably a phosphoric acid amido group having 1 to 30 carbon atoms, more preferably 1 to 20 carbon atoms, and most preferably 1 to 12 carbon atoms, e.g., diethylphosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, a heterocyclic group (preferably a heterocyclic group having 1 to 30 carbon atoms, and more preferably 1 to 12 carbon atoms; as hetero atoms, e.g., nitrogen, oxygen, sulfur; and specifically, e.g., imidazolyl, pyridyl, quinolyl, furyl, thienyl, piperidyl, morpholino, benzoxazolyl, benzimidazolyl, benzothiazolyl, carbazolyl, azepinyl), a silyl group (preferably a silyl group having 3 to 40 carbon atoms, more preferably 3 to 30 carbon atoms, most preferably 3 to 24 carbon atoms, e.g., trimethylsilyl, triphenylsilyl).

The substituent that $L^{11}$, $L^{13}$ and $L^{14}$ may have is preferably an alkyl group, an aryl group, or a heteroaryl group; more preferably an alkyl group having 1 to 4 carbon atoms, a phenyl group, a biphenyl group, a naphthyl group, an anthryl group, a pyridyl group, or a carbazolyl group; and still more preferably a methyl group, a t-butyl group, or a phenyl group.

$L^{12}$ represents an o-arylene group, an o-heteroarylene group, a vinylene group, or an ethylene group.

$L^{12}$ is preferably an o-arylene group, more preferably an o-phenylene, a 2,3-naphthylene group, or a 2,3-anthrylene group; and still more preferably an o-phenylene group.

$L^{12}$ may have a substituent. Examples of the substituent that $L^{12}$ may have include substituents of the above Group A substituents.

The substituent that $L^{12}$ may have is preferably an alkyl group, an aryl group, or a heteroaryl group; more preferably an alkyl group having 1 to 4 carbon atoms, a phenyl group, a biphenyl group, a naphthyl group, an anthryl group, a pyridyl group, or a carbazolyl group; and still more preferably a methyl group, a t-butyl group, or a phenyl group.

$L^{15}$ represents a trivalent or higher aromatic ring or a trivalent or higher aromatic heterocyclic ring.

$L^{15}$ is preferably a trivalent benzene ring group, a trivalent naphthalene ring group, a trivalent anthracene ring group, a trivalent pyridine ring group, a pyrimidine ring group, a pyrrole ring group, or a carbazole ring group; more preferably a benzene ring, or a pyridine ring group; and most preferably a benzene ring group.

$L^{15}$ may have a substituent. Examples of the substituent that $L^{15}$ may have include substituents of the above Group A substituents. The substituent that $L^{15}$ may have is preferably an alkyl group, an aryl group, or a heteroaryl group; more preferably an alkyl group having 1 to 4 carbon atoms, a phenyl group, a biphenyl group, a naphthyl group, an anthryl group, a pyridyl group, or a carbazolyl group; and still more preferably a methyl group, a t-butyl group, or a phenyl group.

The compound represented by formula (1) may be a low molecular compound, or an oligomer compound, or a polymer compound (mass average molecular mass (converted to polystyrene) of which is preferably from 1,000 to 5,000,000, more preferably from 2,000 to 1,000,000, most preferably from 3,000 to 100,000). In the case of a polymer compound, the structure represented by formula (1) may be present in the main chain or in a side chain of the polymer. Further, in the case of a polymer compound, the compound may be a homopolymer compound or a copolymer compound. The compound according to the present invention is preferably a low molecular compound.

Examples of the compounds of formula (1) are shown below, but the invention is not limited to theses.

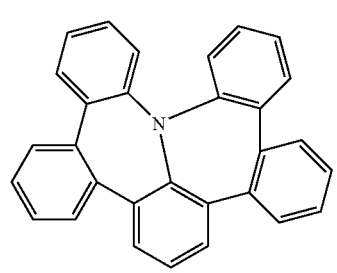

(1-1)

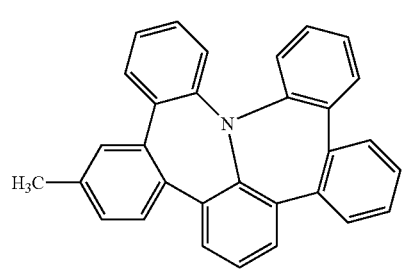

(1-2)

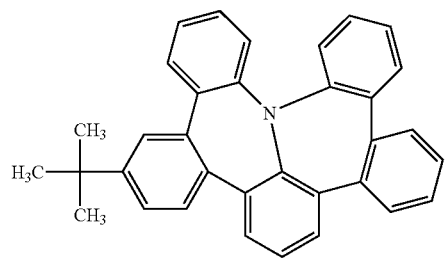

(1-3)

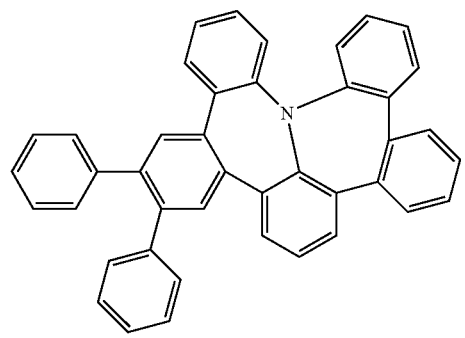

(1-4)

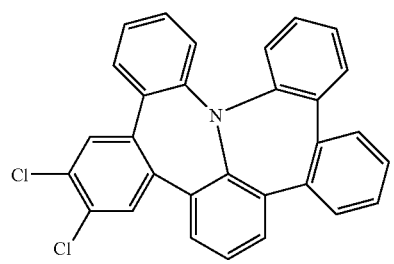

(1-5)

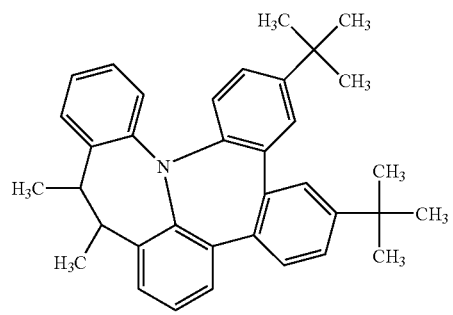

(1-6)

-continued
(1-7) 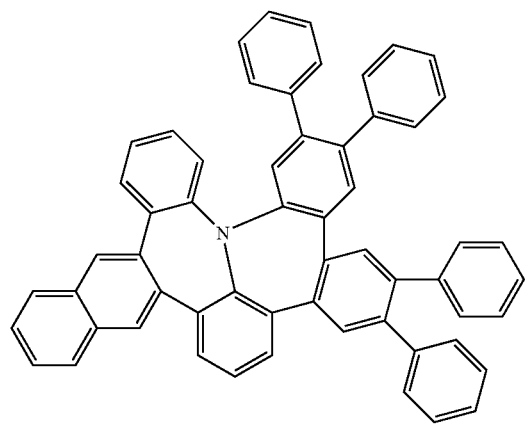
(1-8) 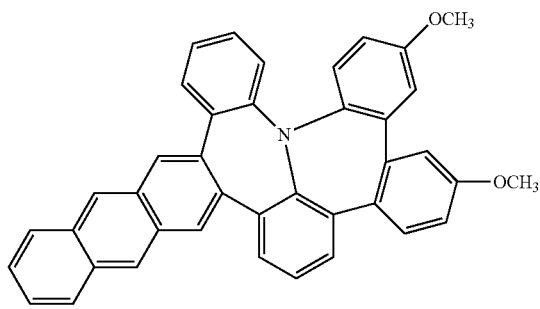
(1-9) 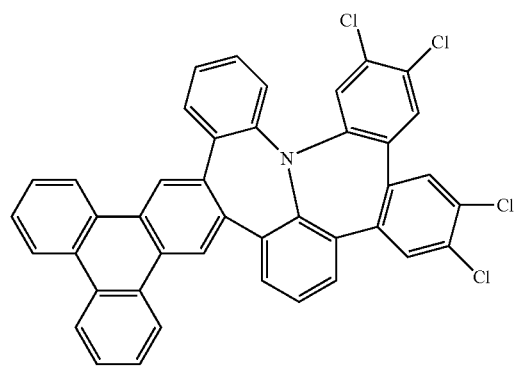
(1-10) 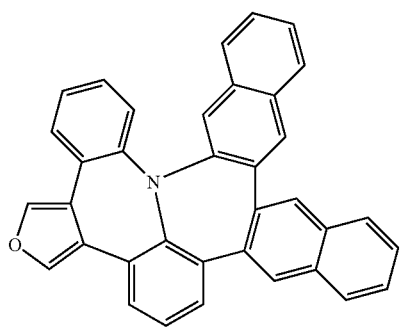
(1-11) 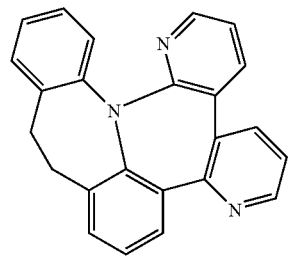
(1-12) 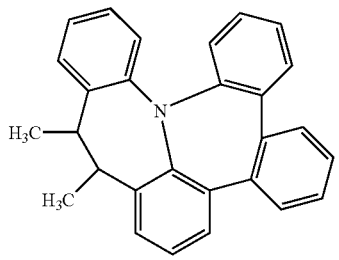
(1-13) 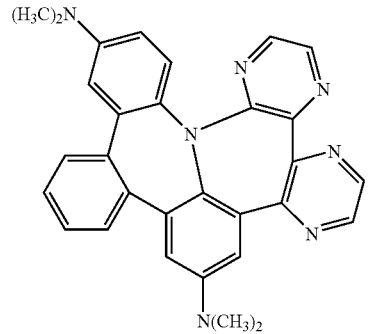
(1-14) 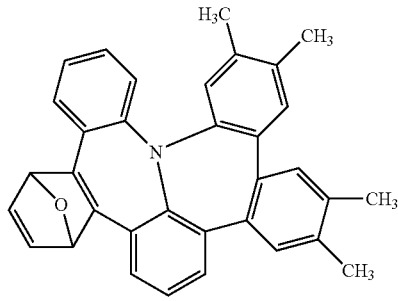

-continued
(1-15)
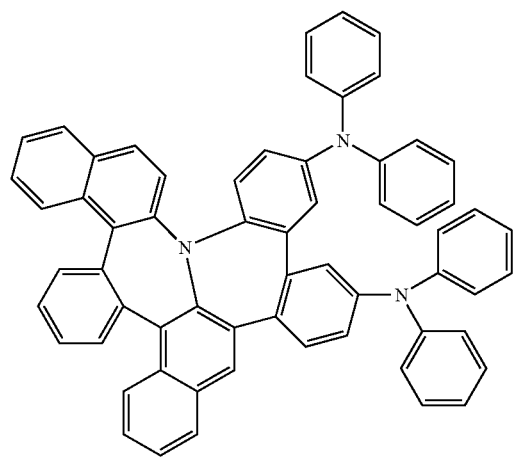
(1-16)
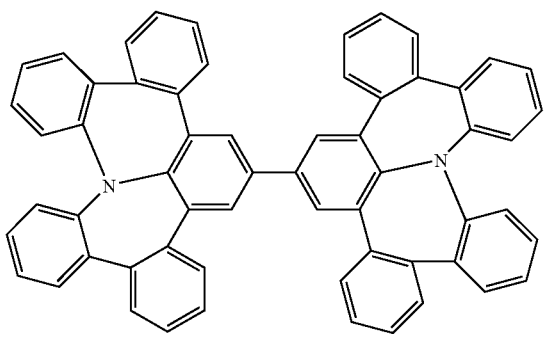
(1-17)
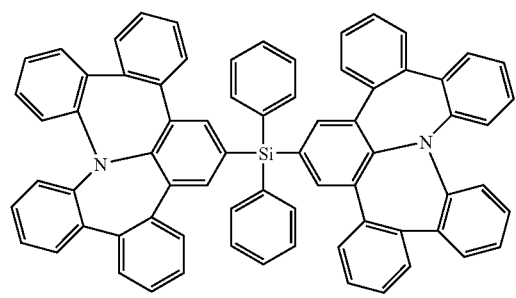
(1-18)
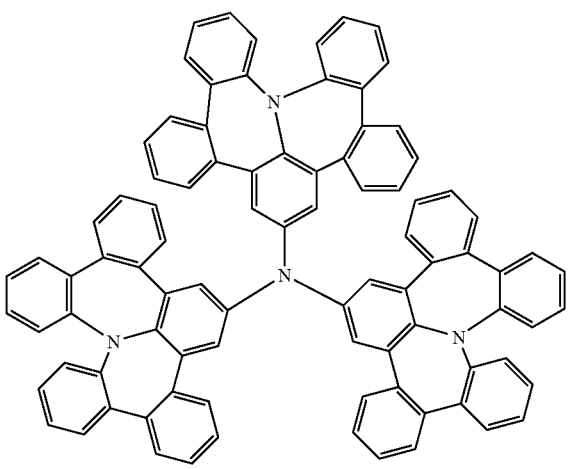
(1-19)
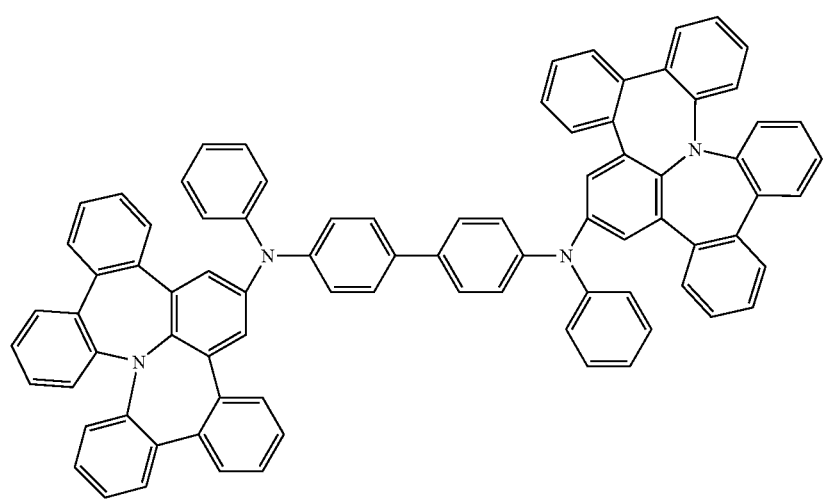

-continued (1-20)

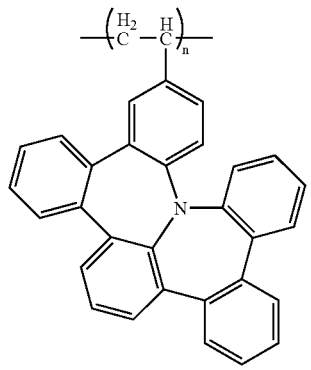

In the organic electroluminescent device of the present invention, the compounds represented by formula (1) are preferably compounds represented by formula (2).

The compounds represented by formula (2) will be explained.

Formula (2)

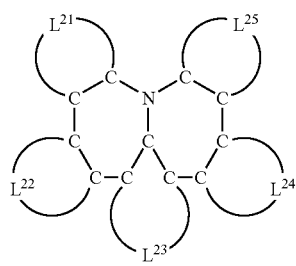

wherein $L^{21}$, $L^{22}$, $L^{23}$, $L^{24}$, and $L^{25}$ each independently represent a group necessary for forming an aromatic ring or a group necessary for forming an aromatic heterocyclic ring.

Each of $L^{21}$, $L^{22}$, $L^{23}$, $L^{24}$, and $L^{25}$ included in formula (2) is independently a group necessary for forming an aromatic ring or a group necessary for forming an aromatic heterocyclic ring. The ring that each of $L^{21}$, $L^{22}$, $L^{23}$, $L^{24}$, and $L^{25}$ forms is preferably a benzene ring, a naphthalene ring, an anthracene ring, a pyridine ring, a pyrimidine ring, a pyrrole ring, or a carbazole ring; more preferably a benzene ring, or a pyridine ring; most preferably a benzene ring.

Each of $L^{21}$, $L^{22}$, $L^{23}$, $L^{24}$, and $L^{25}$ may have a substituent. Examples of the substituent that $L^{21}$, $L^{22}$, $L^{23}$, $L^{24}$ and $L^{25}$ may have include substituents of the above Group A substituents.

The substituent that $L^{21}$, $L^{22}$, $L^{23}$, $L^{24}$, and $L^{25}$ may have is preferably an alkyl group, an aryl group, or a heteroaryl group; more preferably an alkyl group having 1 to 4 carbon atoms, a phenyl group, a biphenyl group, a naphthyl group, an anthryl group, a pyridyl group, or a carbazolyl group; and still more preferably a methyl group, a t-butyl group, or a phenyl group.

Examples of the compounds of formula (2) include compounds (1-1) to (1-5), (1-7) to (1-10), (1-13), and (1-15) to (1-19), among the above compounds which are described as examples of the compounds of formula (1), but the present invention shall not be limited thereto.

The compounds of the present invention have a specific molecular form in which a nitrogen atom is covered with aromatic rings. When a compound is oxidized, it follows that its nitrogen atom is oxidized first. However, it is assumed that the compounds of the present invention have high stability against oxidation since the oxidation center is shielded from the outside.

In a light-emitting device, electric oxidation-reduction is constantly repeated, and devices using the compounds according to the present invention hence exhibit high durability and can have increased lifetimes.

Another embodiment of the present invention is a compound represented by the above formula (2).

The luminescent device (hereinafter referred to also as a light-emitting device) of the present invention will be explained. The light-emitting device of the present invention is not particularly limited with respect to the system, driving method, and utilization form so far as it is a device utilizing the compound of formula (1) or (2). The compounds of formula (1) or (2) can also be applied to other light-emitting devices different from organic EL (electroluminescence) devices.

In the light-emitting device of the present invention, the at least one organic layer comprising the compound of formula (1) is preferably a hole-transporting layer or a luminescent layer, and more preferably a luminescent layer. Most preferably, the compound is contained as a host material in a luminescent layer.

When the compound of formula (1) is contained in a hole-transporting layer, the concentration of the compound of formula (1) is preferably 30 mass % or more but 100 mass % or less, more preferably 60 mass % or more but 100 mass % or less, and further more preferably 90 mass % or more but 100 mass % or less. When the compound of formula (1) is contained in a luminescent layer, the concentration of the compound of formula (1) is preferably 10 mass % or more but 99 mass % or less, more preferably 40 mass % or more but 98 mass % or less, and further more preferably 70 mass % or more but 95 mass % or less.

In the luminescent device of the present invention, the luminescent material contained in the light-emitting layer may be a fluorescence-emitting compound or a phosphorescence-emitting compound. Examples of the luminescent material include benzoxazole and derivatives thereof, benzimidazole and derivatives thereof, benzthiazole and derivatives thereof, styrylbenzene and derivatives thereof, polyphenyl and derivatives thereof, diphenylbutadiene and derivatives thereof, tetraphenylbutadiene and derivatives thereof, naphthalimide and derivatives thereof, coumarin and derivatives thereof, condensed aromatic compounds, perynone and derivatives thereof, oxadiazole and derivatives thereof, oxazine and derivatives thereof, aldazine and derivatives thereof, pyralidine and derivatives thereof, cyclopentadiene and derivatives thereof, bisstyrylanthracene and derivatives thereof, quinacridon and derivatives thereof, pyrrolopyridine and derivatives thereof, thiadiazolopyridine and derivatives thereof, cyclopentadiene and derivatives thereof, styrylamine and derivatives thereof, diketopyrrolopyrrole and derivatives thereof, aromatic dimethylidyne and derivatives thereof; various metal complexes, typical examples of which include metal complexes of 8-quinolinol and derivatives thereof, metal complexes of pyrromethene and derivatives thereof, rare earth element complexes, and transition metal complexes; polymer compounds such as polythiophene, polyphenylene, and polyphenylenevinylene; and organic silane compounds and derivatives thereof. The luminescent material is preferably selected from condensed aromatic compounds, quinacridon and derivatives thereof, diketopyrrolopyrrole and derivatives thereof, metal complexes of pyrromethene and derivatives thereof, rare earth element complexes, and transition metal complexes, and is more preferably selected from condensed aromatic compounds and transition metal complexes.

When the compound of formula (1) according to the present invention is contained in the light-emitting layer as a host material, the host material may also serve as a luminescent material.

When the luminescent material is a phosphorescence-emitting compound, the luminescent material is particularly preferably a transition metal complex. The central metal of the transition metal complex is not particularly limited, but is preferably iridium, platinum, rhenium, or ruthenium, more preferably iridium or platinum, most preferably iridium. Of the transition metal complexes, orthometalated complexes are preferred. The term "orthometalated complex" is a general term for a group of compounds described in "Yuki Kinzoku, Kiso To Oyo", written by Akio Yamamoto and published by Shokabo Sha in 1982, p. 150 and p. 232; and "Photochemistry and Photophysics of Coordination Compound" written by H. Yersin and published by Springer-Verlag in 1987, pp. 71 to 77 and pp. 135 to 146.

The phosphorescence material has a phosphorescence quantum yield at 20° C. or higher of preferably 70% or more, more preferably 80% or more, most preferably 85% or more.

As the phosphorescence-emitting material, there may be utilized, for example, those described in patent literature such as U.S. Pat. Nos. 6,303,231 B1, 6,097,147, WO 00/57676, WO 00/70655, WO 01/08230, WO 01/39234 A2, WO 01/41512 A1, WO 02/02714 A2, WO 02/15645 A1, JP-A-2001-247859, JP-A-2002-302671 (Japanese Patent Application No. 2000-33561), JP-A-2002-117978 (Japanese Patent Application No. 2001-189539), JP-A-2003-133074 (Japanese Patent Application No. 2001-248165), JP-A-2002-235076 (Japanese Patent Application No. 2001-33684), Japanese Patent Application No. 2001-239281, JP-A-2002-170684 (Japanese Patent Application No. 2001-219909), EP 1211257, JP-A-2002-226495, JP-A-2002-234894, JP-A-2001-247859, JP-A-2001-298470, JP-A-2002-173674, JP-A-2002-203678, JP-A-2002-203679; and non-patent literature such as Nature, vol. 395, p. 151 (1998), Applied Physics Letters, vol. 75, p. 4 (1999), Polymer Preprints, vol. 41, p. 770 (2000), Journal of American Chemical Society, vol. 123, p. 4304 (2001), Applied Physics Letters, vol. 79, p. 2082 (1999).

The formation method of the organic layer (organic compound layer) of the light-emitting device containing the compound according to the present invention is not particularly limited but includes resistance heating vapor deposition, electron beam irradiation, sputtering, molecular lamination method, coating methods, inkjet method, printing method, and transfer method. Above all, resistance heating vapor deposition, coating method, and transfer method are preferable from the standpoints of characteristics and manufacture.

The light-emitting device of the present invention may be a device in which at least one organic layer (organic compound layer) is formed between a pair of electrodes, an anode and a cathode, and may further have a hole-injecting layer, a hole-transporting layer, an electron-injecting layer, an electron-transporting layer, a protective layer, and the like, in addition to the light-emitting layer. Each of these layers may be provided with another function. Various materials may be used for the formation of the respective layers.

The substrate material of the light-emitting device of the present invention, is not particularly limited, and examples thereof include inorganic materials such as zirconia-stabilized yttrium, glass, and the like; and macromolecular (high molecular) materials such as polyesters (for example, polyethylene terephthalate, polybutylene terephthalate, and polyethylene naphthalate), polyethylenes, polycarbonates, polyethersulfones, polyarylates, allyldiglycolcarbonates, polyimides, polycycloolefins, norbornene resins, poly(chlorotrifluoroethylene), Teflon (registered trade mark), and polytetrafluoroethylene-polyethylene copolymers, and the like.

The anode supplies holes to the hole-injecting layer, the hole-transporting layer, the light-emitting layer, and the like. The anode may be formed of metals, alloys, metal oxides, electric conductive compounds, mixtures thereof, and the like, preferably materials having a work function of 4 eV or more. Examples thereof include conductive metal oxides such as tin oxide, zinc oxide, indium oxide, indium tin oxide (ITO), and the like; metals such as gold, silver, chromium, nickel, and the like; further mixtures or laminates of the metals with the conductive metal oxides; inorganic conductive materials such as copper iodide, copper sulfide, and the like; organic conductive materials such as polyaniline, polythiophene, polypyrrole, and the like; and laminates thereof with ITO. Conductive metal oxides are preferred, and ITO is particularly preferred in terms of productivity, high conductivity, and transparency. The thickness of the anode may be appropriately selected depending on the kind of material, and is preferably from 10 nm to 5 μm, more preferably from 50 nm to 1 μm, and most preferably from 100 nm to 500 nm.

As the anode, one in which layer formation is carried out on soda-lime glass, on non-alkali glass, or on a transparent resin substrate is usually used. When glass is used, non-alkali glass is preferably used for decreasing ions eluted from glass. When soda lime-glass is used, it is preferable to use one provided with a barrier coat of silica or the like. There is no particular limitation on the thickness of the substrate, as long as it is sufficient to keep mechanical strength. When glass is used, the thickness is usually 0.2 mm or more, and preferably 0.7 mm or more.

Various methods are used for the preparation of the anodes depending on the kind of material. For example, in the case of ITO, film formation may be carried out by methods such as electron beam processing, sputtering, resistance heating vapor deposition, chemical reaction (sol-gel processing), coating of a dispersion of indium tin oxide, and the like.

By subjecting the anode to treatments such as washing and others, the driving voltage for the light-emitting device may be reduced and the luminance efficiency may be raised. For example, in the case of ITO, UV-ozone treatment and plasma treatment are effective.

The cathode supplies electrons to the electron-injecting layer, the electron-transporting layer, the light-emitting layer, and the like. The cathode may be selected considering ionization potential, stability, and adhesion to layers adjacent to the negative electrode, such as the electron-injecting layer, the electron-transporting layer, and the light-emitting layer. As materials for the cathodes, metals, alloys, metal halides, metal oxides, electric conductive compounds, or mixtures thereof may be used. Examples thereof include alkali metals (for example, Li, Na, K) or fluorides and oxides thereof, alkali earth metals (for example, Mg and Ca) or fluorides and oxides thereof, gold, silver, lead, aluminum, sodium-potassium alloys or mixed metals thereof, lithium-aluminum alloys or mixed metals thereof, magnesium-silver alloys or mixed metals thereof, and rare earth metals such as indium and ytterbium. Materials having a work function of 4 eV or less are preferred, more preferably aluminum, lithium-aluminum alloys or mixed metals thereof, magnesium-silver alloys or mixed metals thereof, or the like. The cathode may have a single layer structure of any of the above-mentioned compounds and mixtures, or an accumulated layer structure containing any of the above-mentioned compounds and mixtures. For example, accumulated layer structures of aluminum/lithium fluoride and aluminum/lithium oxide are preferable. The film thickness of the cathode can be appropriately selected depending on the material, and is preferably from 10 nm to 5 μm, more preferably from 50 nm to 1 μm, and further preferably from 100 nm to 1 μm.

For the preparation of the cathodes, methods such as electron beam processing, sputtering, resistance heating vapor deposition, and coating are used. The metals may be vapor deposited as simple substances, or two or more components may be vapor deposited at the same time. Further, it is also possible to vapor deposit a plurality of metals at the same time to form an alloy electrode, or an alloy previously prepared may also be vapor deposited.

The anode and the cathode each preferably have low sheet resistance, particularly have a sheet resistance of several hundred $\Omega/\square$ (ohms per square) or less.

Materials for the luminescent layer (hereinafter referred to also as light-emitting layer) may be any materials, as long as they can form layers having the function of being able to inject, upon electric field application, holes from the anode, the hole-injecting layer, or the hole-transporting layer, and inject electrons from the cathode, the electron-injecting layer, or the electron-transporting layer; the function of transporting injected charges; or the function of providing the field of recombination of holes with electrons to emit light. Examples include benzoxazole, benzimidazole, benzothiazole, styrylbenzene, polyphenyl, diphenylbutadiene, tetraphenylbutadiene, naphthalimide, coumarin, perylene, perynone, oxadiazole, aldazine, pyralizine, cyclopentadiene, bis(styryl)anthracene, quinacridone, pyrrolopyridine, thiadiazolopyridine, cyclopentadiene, styrylamine, aromatic dimethylidyne compounds, various metal complexes represented by metal complexes or rare earth element complex of 8-quinolinol; and polymer compounds such as polythiophene, polyphenylene, polyphenylenevinylene; organic silane compounds, tris(phenylpyridine)iridium complex, transition metal complexes represented by porphyrin platinum complexes, the derivatives thereof, the compounds of the present invention, and the like. The light-emitting layer includes at least one phosphorescence material. Although there is no particular limitation on the thickness of the light-emitting layer, it is usually preferably from 1 nm to 5 μm, more preferably from 5 nm to 1 μm, and most preferably from 10 nm to 500 nm.

Although there is no particular limitation on methods for forming the light-emitting layer, methods such as resistance heating vapor deposition, electron beam processing, sputtering, molecular lamination, coating (spin coating, casting, and dip coating), inkjet process, printing, LB processing, and transfer method may be used. Preferred are resistance heating vapor deposition and coating.

The luminescent layer may be made of a single compound or plural compounds. The luminescent layer can be formed as a single layer or plural layers. The layers may emit rays in different colors, so as to emit, for example, a white ray, or the single luminescent layer may emit a white ray. In the case of the plural luminescent layers, each of the luminescent layers may be made of a single material or plural compounds.

The luminescent layer of the organic electroluminescent device of the present invention may have at least one layered-structure. The number of layers in this structure is preferably from 2 to 50, more preferably from 4 to 30, and most preferably from 6 to 20.

The thickness of each of the layers constituting the layered structure is not particularly limited, but it is preferably from 0.2 nm to 20 nm, more preferably from 0.4 nm to 15 nm, even more preferably from 0.5 nm to 10 nm, and most preferably from 1 nm to 5 nm.

The luminescent layer of the organic electroluminescent device of the invention may have plural domain structures. The luminescent layer may contain therein some other domain structure. The diameter of each of the domain structures is preferably from 0.2 nm to 10 nm, more preferably from 0.3 nm to 5 nm, even more preferably from 0.5 nm to 3 nm, and most preferably from 0.7 nm to 2 nm.

Materials for the hole-injecting layers and the hole-transporting layers may be any materials, as long as they have any of the function of injecting holes from the anode, the function of transporting holes, and the function of blocking electrons injected from the cathode. Examples thereof include carbazole, triazole, oxazole, oxadiazole, imidazole, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, aromatic dimethylidyne compounds, porphyrin compounds, polysilane compounds, poly(N-vinylcarbazole), aniline copolymers, thiophene oligomers, conductive high molecular oligomers such as polythiophene; organic silane derivatives, carbon film, and the compounds of the present invention, phthalocyanine (metallophthalocyanine), and the derivatives thereof, and the like. Although there is no particular limitation of the thickness of the hole-injecting layer and the hole-transporting layer, it is usually preferably from 1 nm to 5 μm, more preferably from 5 nm to 1 μm, and most preferably from 10 nm to 500 nm. The hole-injecting layer and the hole-transporting layer may have either a monolayer structure comprising one or more kinds of the above-mentioned materials, or a multilayer (accumulated layer) structure having a plurality of layers each comprising the same composition or different compositions.

As methods for forming the hole-injecting layers and the hole-transporting layers, vacuum deposition, LB processing, coating (spin coating, casting, and dip coating) of the above-mentioned materials for the hole-injecting layers and the hole-transporting layers dissolved or dispersed in solvents, inkjet process, printing, and transfer method are used. In the case of coating, the materials may be dissolved or dispersed together with a resin component. Examples of the resin component include polyvinyl chlorides, polycarbonates, polystyrenes, polymethyl methacrylates, polybutyl methacrylates, polyesters, polysulfones, polyphenylene oxides, polybutadienes, poly(N-vinylcarbazole)s, hydrocarbon resins, ketone resins, phenoxy resins, polyamides, ethyl cellulose, vinyl acetate, ABS resins, polyurethanes, melamine resins, unsaturated polyester resins, alkyd resins, epoxy resins, and silicone resins.

Materials for the electron-injecting layers and the electron-transporting layers may be any materials, as long as they have any of the function of injecting electrons from the cathode, the function of transporting electrons, and the function of blocking holes injected from the anode. Examples thereof include triazole, oxazole, oxadiazole, imidazole, fluorenone, anthraquinodimethane, anthrone, diphenylquinone, thiopyran dioxide, carbodiimide, fluorenylidenemethane, distyrylpyrazine, naphthalene, tetracarboxylic acid anhydrides of aromatic rings such as naphthalene and perylene; phthalocyanine, various metal complexes represented by metal complexes of 8-quinolinol, metallophthalocyanine, and metal complexes each having benzoxazole or benzothiazole as a ligand, organic silane, the compounds of the present invention, and the derivatives thereof. Although there is no particular limitation of the thickness of the electron-injecting layer and the electron-transporting layer, it is usually preferably from 1 nm to 5 µm, more preferably from 5 nm to 1 µm, and most preferably from 10 nm to 500 nm. The electron-injecting layer and the electron-transporting layer may have either a monolayer structure comprising one kind or two or more kinds of the above-mentioned materials, or a multilayer (an accumulated layer) structure having a plurality of layers each comprising the same composition or different compositions.

As methods for forming the electron-injecting layers and the electron-transporting layers, vacuum deposition, LB processing, coating (spin coating, casting, and dip coating) of the above-mentioned materials for the electron-injecting layers and the electron-transporting layers dissolved or dispersed in solvents; inkjet process, printing, transfer are used. In the case of coating, the materials can be dissolved or dispersed together with a resin component. As the resin component, for example, ones illustrated in the case of the hole-injecting layers and the hole-transporting layers can be applied.

Materials for the protective layer may be any materials, as long as they have the function of inhibiting promoters of device deterioration such as water and oxygen from entering the devices. Examples thereof include metals such as In, Sn, Pb, Au, Cu, Ag, Al, Ti, and Ni; metal oxides such as MgO, SiO, $SiO_2$, $Al_2O_3$, GeO, NiO, CaO, BaO, $Fe_2O_3$, $Y_2O_3$, and $TiO_2$; metal fluorides such as $MgF_2$, LiF, $AlF_3$, and $CaF_2$; nitrides such as $SiN_x$ and $SiO_xN_y$; polyethylene, polypropylene, polymethyl methacrylate, polyimides, polyureas, polytetrafluoroethylene, polychlorotrifluoroethylene, polydichlorodifluoroethylene, copolymers of chlorotrifluoroethylene and dichlorodifluoroethylene, copolymers obtained by copolymerizing monomer mixtures each containing tetrafluoroethylene and at least one kind of comonomer, fluorine-containing copolymers having cyclic structures on main chains of the copolymers, water-absorptive substances having a water absorption of 1% or more, and moisture-proof substances having a water absorption of 0.1% or less.

There is no particular limitation on methods for forming the protective layers. For example, vacuum deposition, sputtering, reactive sputtering, MBE (molecular beam epitaxy), cluster ion beam processing, ion plating, plasma polymerization (high-frequency excitation ion plating), plasma CVD, laser CVD, thermal CVD, gas source CVD, coating, inkjet process, printing, and transfer can be applied.

The light-extraction efficiency in the luminescent device of the present invention may be improved by various conventional techniques. For example, surface structuring of the substrate (for example, formation of a fine concavo-convex pattern), controlling the refractive index of the substrate, ITO layer, or organic layer(s), and controlling the thickness of the substrate, ITO layer, or organic layer(s). These improvements may lead to increase light-extraction efficiency and external quantum efficiency.

The light-emitting device of the present invention may be of a so-called top emission type, in which light is emitted from the anode side of the device.

Another embodiment of the present invention is a method for producing a compound represented by formula (5), which includes reacting a compound represented by formula (3) with a compound represented by formula (4) (sometimes referred to as "Production Method I of the present invention" hereinafter).

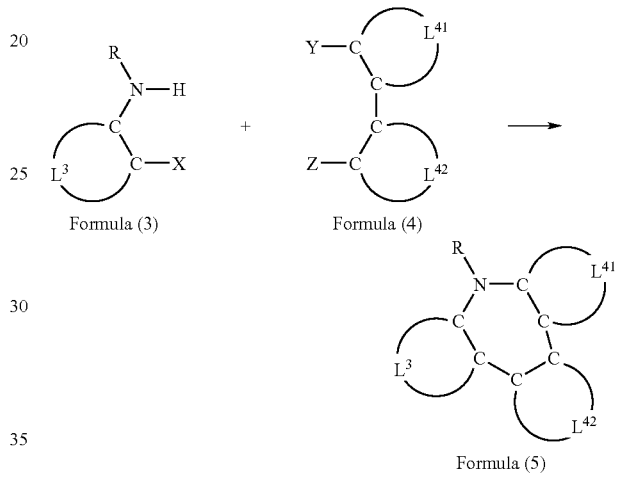

Formula (3)    Formula (4)

Formula (5)

In the above formulae, $L^3$, $L^{41}$, and $L^{42}$ each independently represent a group necessary for forming an aromatic ring or a group necessary for forming an aromatic heterocyclic ring. X, Y, and Z each independently represent a hydrogen atom or a group that splits off in the reaction, and at least one of Y and Z is a halogen atom or a group that splits off in the reaction. R represents a hydrogen atom or a substituent.

The compounds represented by the above formulae (3), (4), and (5) will be explained.

In formulae (3), (4) and (5), each of $L^3$, $L^{41}$, and $L^{42}$ is independently a group necessary for forming an aromatic ring or a group necessary for forming an aromatic heterocyclic ring.

The ring that each of $L^3$, $L^{41}$, and $L^{42}$ forms is preferably a benzene ring, a naphthalene ring, an anthracene ring, a pyridine ring, a pyrimidine ring, a pyrrole ring, or a carbazole ring, more preferably a benzene ring or a pyridine ring, and most preferably a benzene ring.

Each of $L^3$, $L^{41}$, and $L^{42}$ may have a substituent. Examples of the substituent that $L^3$, $L^{41}$, and $L^{42}$ may have include substituents of the above Group A substituents. The substituent that $L^3$, $L^{41}$, and $L^{42}$ may have is preferably an alkyl group, an aryl group, or a heteroaryl group; more preferably an alkyl group having 1 to 4 carbon atoms, a phenyl group, a biphenyl group, a naphthyl group, an anthryl group, a pyridyl group, or a carbazolyl group; and still more preferably a methyl group, a t-butyl group, or a phenyl group.

Each of X, Y, and Z is independently a hydrogen atom or a group that splits off in the reaction.

The group that splits off in the reaction is preferably a halogen atom, a sulfonyl group, a trifluoromethyl group, or a trifluorobutyl group; more preferably a bromine atom, an iodine atom, a trifluoromethyl group, or a trifluorobutyl group; and still more preferably a bromine atom or an iodine atom.

However, at least one of Y and Z is a halogen atom or a group that splits off in the reaction.

R represents a hydrogen atom or a substituent. Examples of the substituent include substituents shown in the above Group A substituents. R is preferably a hydrogen atom, an alkyl group, an aryl group, or a heteroaryl group, more preferably an alkyl group having 1 to 4 carbon atoms, a phenyl group, a biphenyl group, a naphthyl group, an anthryl group, a pyridyl group, or a carbazolyl group; and still more preferably a methyl group or a phenyl group.

It is considered that the reaction in Production Method I of the present invention proceeds according to the following mechanism.

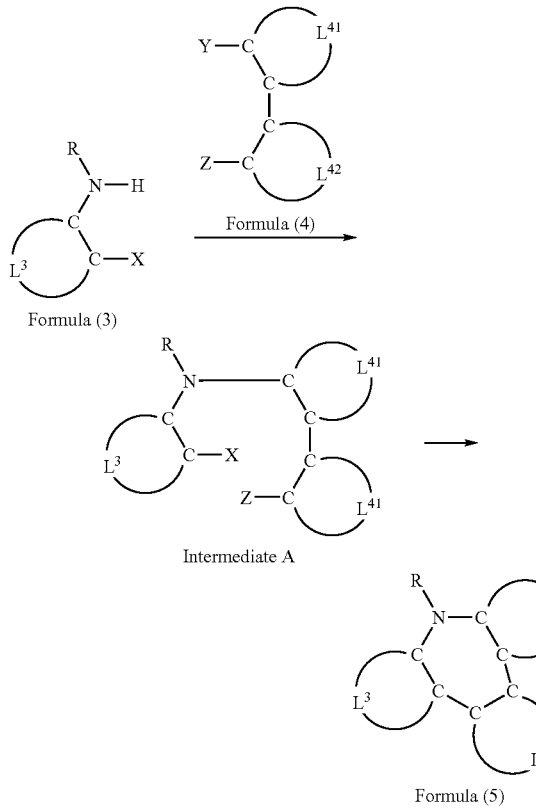

Formula (3)

Formula (4)

Intermediate A

Formula (5)

First, a nitrogen-carbon bond is formed between a compound of formula (3) and a compound of formula (4) to generate an intermediate A, and then a ring formation reaction takes place in the molecule of the intermediate A to generate a compound of formula (5).

In the above reaction, the formation of the nitrogen-carbon bond between the compound of formula (3) and the compound of formula (4) can be carried out by utilizing various known carbon-nitrogen bonding reactions. The method therefor is not particularly limited, but is preferably, for example, a synthesizing method using a palladium catalyst, as described in "Journal of American Chemical Society", 118, 7215 (1996), "Journal of American Chemical Society", 118, 7217 (1996), or some other document.

Examples of the palladium catalysts include, but are not limited to, palladium tetrakis(triphenylphosphine), palladium-carbon, palladium acetate, and palladium dichloride (dppf) (dppf: 1,1'-bisdiphenylphosphinoferrocene). Ligands such as triphenylphosphine and $P(t-Bu)_3$ may be added at the same time.

In the present reaction, it is preferable to use a base. The kind of the base is not particularly limited, and examples thereof include sodium carbonate, sodium acetate, potassium carbonate, rubidium carbonate, triethylamine, sodium t-butoxide, and potassium t-butoxide. The amount of the base is not particularly limited, and is preferably from 0.1 to 20 equivalents, more preferably from 1 to 10 equivalents to a compound represented by formula (3).

In this reaction, a solvent is preferably used. Examples of the solvent to be used include, but are not limited to, ethanol, water, ethylene glycol dimethyl ether, diethylene glycol dimethyl ether, dimethylformamide, toluene, tetrahydrofuran, xylene, mesitylene, and mixed solvents thereof.

The reaction temperature when the compound of the invention is synthesized is not particularly limited, but is preferably from 20 to 220° C., more preferably from 20 to 180° C., and most preferably from 20 to 160° C.

Conditions for the ring formation reaction in the molecule of the intermediate A are similar to the conditions under which the nitrogen-carbon bonding reaction takes place between the compound of formula (3) and the compound of formula (4), and preferred ranges of the reaction conditions are also similar to those in the nitrogen-carbon bonding reaction.

Another embodiment of the present invention is a method for producing a compound represented by formula (2), which comprises reacting a compound represented by formula (3a) with a compound represented by formula (4a) (sometimes also referred to as "Production Method II of the present invention" hereinafter).

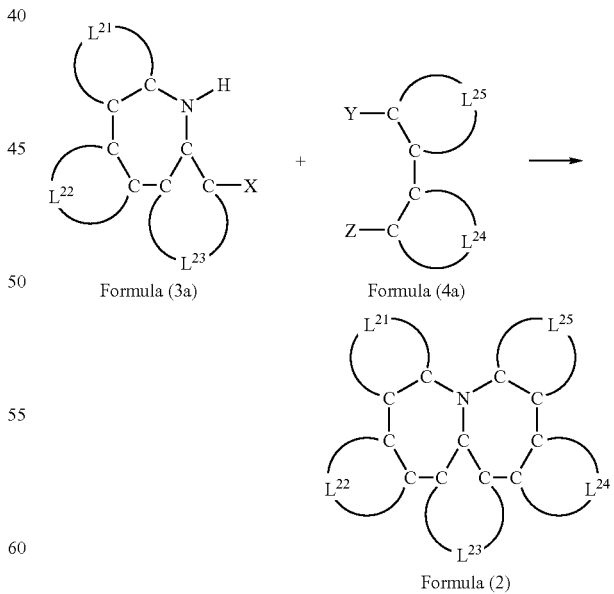

Formula (3a)

Formula (4a)

Formula (2)

In the above formulae, $L^{21}$, $L^{22}$, $L^{23}$, $L^{24}$, and $L^{25}$ each independently represent a group necessary for forming an aromatic ring or a group necessary for forming an aromatic heterocyclic ring. X, Y, and Z each independently represent a hydrogen atom or a group that splits off in the reaction, and at least one of Y and Z is a halogen atom or a group that splits off in the reaction.

$L^{21}$, $L^{22}$, $L^{23}$, $L^{24}$, and $L^{25}$ in formula (3a) or (4a) have the same meanings as those of the aforementioned $L^{21}$, $L^{22}$, $L^{23}$, $L^{24}$, and $L^{25}$ in formula (2), respectively, with the same preferable ranges. X, Y, and Z in formula (3a) or (4a) have the same meanings as those of the aforementioned X, Y, and Z in formula (3) or (4), respectively, with the same preferable ranges.

The above scheme corresponds to the case where R in formula (5) is a hydrogen atom. A compound of formula (2) can be synthesized with using a compound of formula (5) as a starting material.

It is considered that Production Method II of the present invention proceeds according to the same mechanism as that in Production Method I of the present invention. In the above reaction, the formation of the nitrogen-carbon bond between the compound of formula (3a) and the compound of formula (4a) can be carried out by utilizing various known carbon-nitrogen bonding reactions. The method therefor is not particularly limited, and is preferably, for example, a synthesizing method using a palladium catalyst, as described in "Journal of American Chemical Society", 118, 7215 (1996), "Journal of American Chemical Society", 118, 7217 (1996), or some other document, as in the case of the Production Method I of the present invention. Reaction conditions and preferred ranges thereof are the same as those in Production Method I of the present invention. Further, reaction conditions and preferred ranges thereof in the ring formation reaction in the molecule of the intermediate generated in Production Method II of the present invention are also the same as those in Production Method I of the present invention.

The present invention provides an organic electroluminescent device excellent in light-emitting properties, specific azepine compounds, and a method for producing the same.

An organic electroluminescent device according to the present invention that contains at least one compound of the above formula (1) in the above organic layer is excellent in light-emitting properties.

The compounds of the above formula (2) according to the present invention are useful as materials for light-emitting devices excellent in light-emitting properties.

The production method of the present invention can be generally applied to formation of an azepine structure. This method enables forming an azepine structure in very short steps as compared with any conventional method.

The present invention will be described in more detail based on examples given below, but the invention is not meant to be limited by these.

EXAMPLES

Example 1

Synthesis of Compound (A-1)

Under nitrogen current, 8.3 g of 2,2'-dibromobiphenyl, 5.5 g of diphenylaniline, 0.3 g of palladium diacetate, 1 ml of tris-t-butyl phosphine, 10.0 g of sodium-t-butoxide, and 100 ml of xylene were refluxed under heat and stirred for 3 hours. The proceeding of the reaction was traced with TLC (thin-layer chromatography), and the disappearance of the raw materials was thereby confirmed. Then, 50 ml of chloroform and 50 ml of water were added to the reaction mixture, followed by liquid separation. The resultant organic layer was washed with water and liquid-separated. The thus-obtained organic layer was dried over magnesium sulfate and filtered, and then the solvent was distilled off under reduced pressure. The resultant solid was purified by column chromatography (hexane/chloroform) and then recrystallized from a hexane/chloroform mixture solvent, to give 4.5 g of Compound A-1 (yield 52%) and 2.6 g of Compound A-2 (yield 20%).

As describe above, according to the method of the present invention, Compound A-1 having a tribenzazepine structure can be synthesized from commercially available materials through one step. That is, it is clear that the production method of the present invention is remarkably useful as compared with a conventional method that requires multi-steps for forming a tribenzazepine structure as described in JP-A-2001-97953.

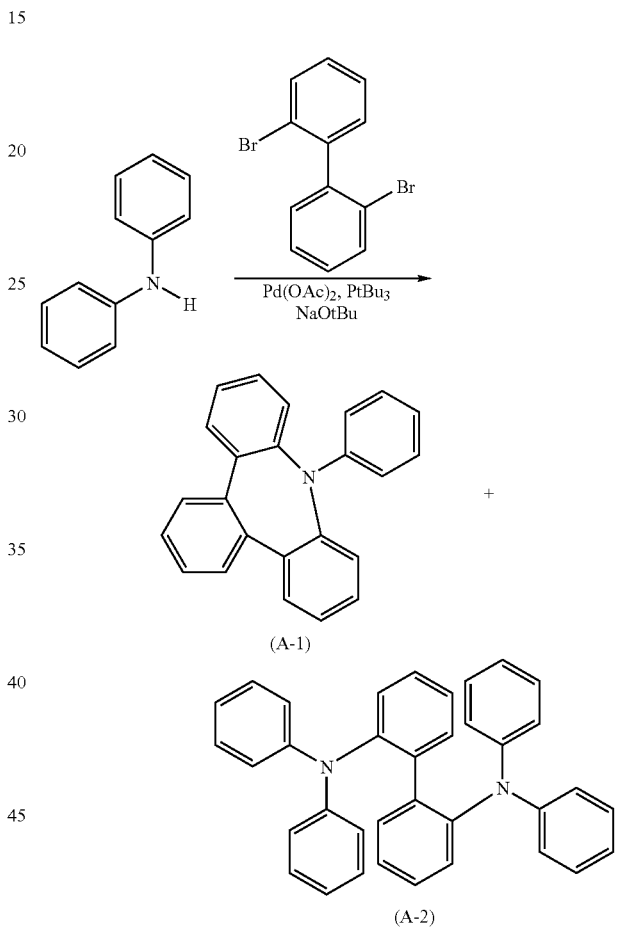

Example 2

Synthesis of Compound (1-1)

Under nitrogen current, 3.0 g of 2,2'-dibromobiphenyl, 2.8 g of Compound B, 0.11 g of palladium diacetate, 0.36 ml of tris-t-butyl phospine, 3.7 g of sodium-t-butoxide, and 50 ml of xylene were refluxed under heat and stirred for 3 hours. The proceeding of the reaction was traced with TLC (thin-layer chromatography), and the disappearance of the raw materials was thereby confirmed. Then, 50 ml of chloroform and 50 ml of water were added to the reaction mixture, followed by liquid separation. The resultant organic layer was washed with water and liquid-separated. The thus-obtained organic layer was dried over magnesium sulfate and filtered, and then the solvent was distilled off under reduced pressure. The resultant solid was recrystallized from a hexane/chloroform mixture solvent, to give 2.7 g of Compound (1-1) (yield 71%). The thus-obtained compound (1-1) was found to have a high resolution mass spectrum data as below, which was well in agreement with a calculated value.

| HRMS: | Found value of Compound (1-1) | 393.1508 |
|---|---|---|
| | Calculated value of $C_{30}H_{19}N_1$ | 393.1517 |

FIG. 1 shows NMR spectrum of the above Compound (1-1) and a partially enlarged view thereof at 6.5 to 7.7 ppm.

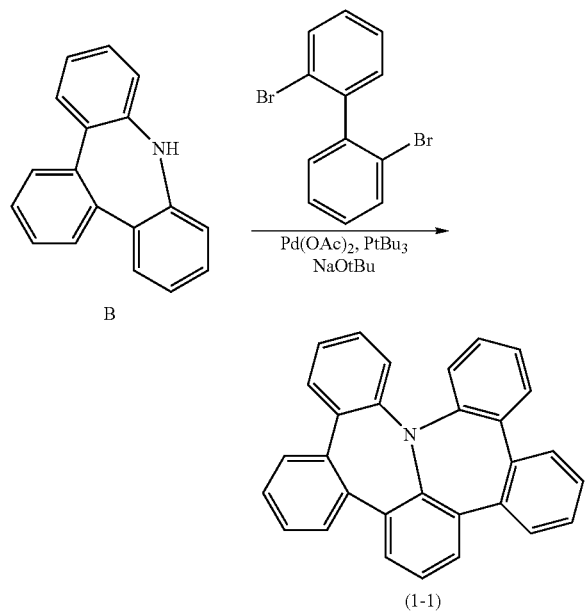

(1-1)

Example 3

Preparation of Organic Electroluminescent Device

A washed ITO substrate was put into a vapor deposition apparatus. First, copper phthalocyanine was vapor-deposited, as a hole-injecting layer, into a thickness of 10 nm on the substrate. Thereon was vapor-deposited α-NPD (N,N'-diphenyl-N,N'-di(α-naphthyl)-benzidine), as a hole-transporting layer, into a thickness of 30 nm. The exemplified compound (1-1) and Ir(ppy)$_3$ were co-vapor-deposited into a thickness of 30 nm, at a ratio (by mass) of 9:1, on the hole-transporting layer. Thereon were successively vapor-deposited BAlq into a thickness of 10 nm and Alq$_3$ into a thickness of 40 nm. A patterned mask (its light-emitting area: 4 mm×5 mm) was set onto the organic thin film, and lithium fluoride was vapor-deposited thereon into a thickness of about 1 nm in the vapor deposition apparatus. Aluminum was vapor-deposited into a thickness of about 200 nm on this lithium fluoride, so as to produce a device. A source measure unit 2400 model, manufactured by Toyo Corporation, was used to apply a constant DC voltage to the EL device, thereby emitting light. The luminance thereof was measured with a luminance meter BM-8 (trade name) manufactured by Topcon Corporation, and the luminescence wavelength thereof was measured with a spectrum analyzer PMA-11 (trade name) manufactured by Hamamatsu Photonics K.K.

As a result, green luminescence having a chromaticity value (0.27, 0.62) was obtained, and the external quantum efficiency of the device was 9.0%.

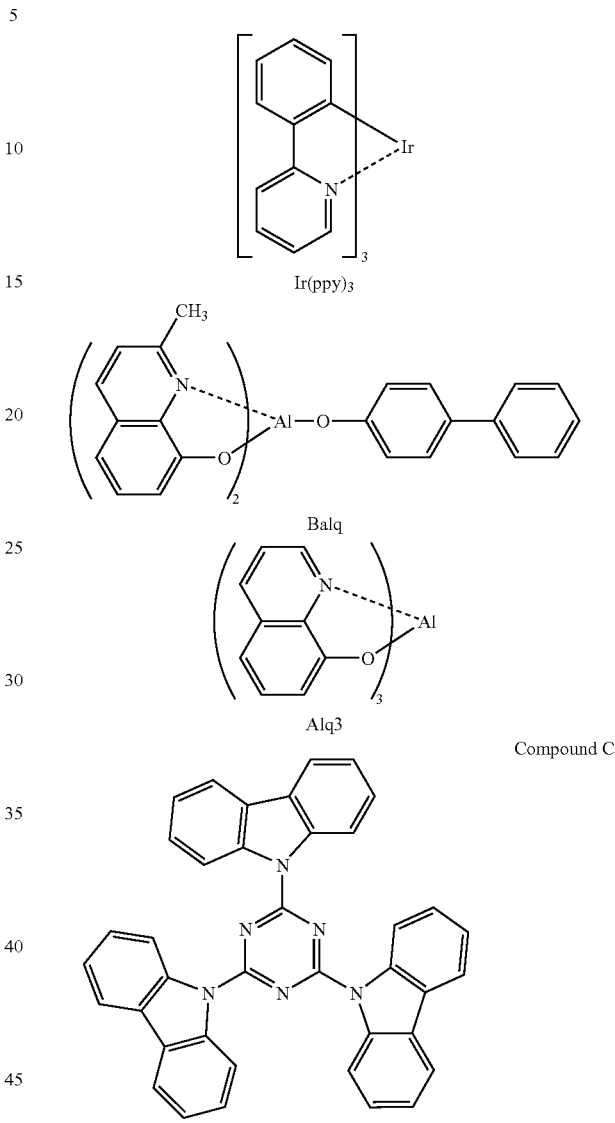

Example 4

A device was prepared and evaluated in the same manner as in Example 3, except that the exemplified compound (1-19) was used instead of α-NPD and Compound C was used instead of the exemplified compound (1-1).

As a result, green luminescence having a chromaticity value (0.27, 0.62) was obtained, and the external quantum efficiency of the device was 8.0%.

Similarly, when other compounds of the present invention are used, high-efficiency light-emission devices can be manufactured.

Having described our invention as related to the present embodiments, it is our intention that the invention not be limited by any of the details of the description, unless otherwise specified, but rather be construed broadly within its spirit and scope as set out in the accompanying claims.

What I claim is:

1. An organic electroluminescent device comprising a pair of electrodes, and at least one organic layer interposed between the pair of electrodes, with the at least one organic layer containing at least one compound represented by formula (2):

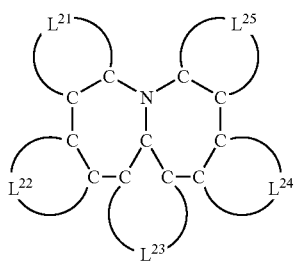

Formula (2)

wherein $L^{21}$, $L^{22}$, $L^{23}$, $L^{24}$, and $L^{25}$ each form a benzene ring.

2. The organic electroluminescent device as claimed in claim 1, wherein the compound represented by formula (2) is contained in a hole-transporting layer or a luminescent layer.

3. A compound represented by formula (2):

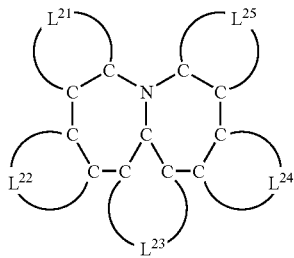

Formula (2)

wherein $L^{21}$, $L^{22}$, $L^{23}$, $L^{24}$, and $L^{25}$ each form a benzene ring.

4. A method for producing a compound represented by formula (2) as claimed in claim 3, which comprises reacting a compound represented by formula (3a) with a compound represented by formula (4a):

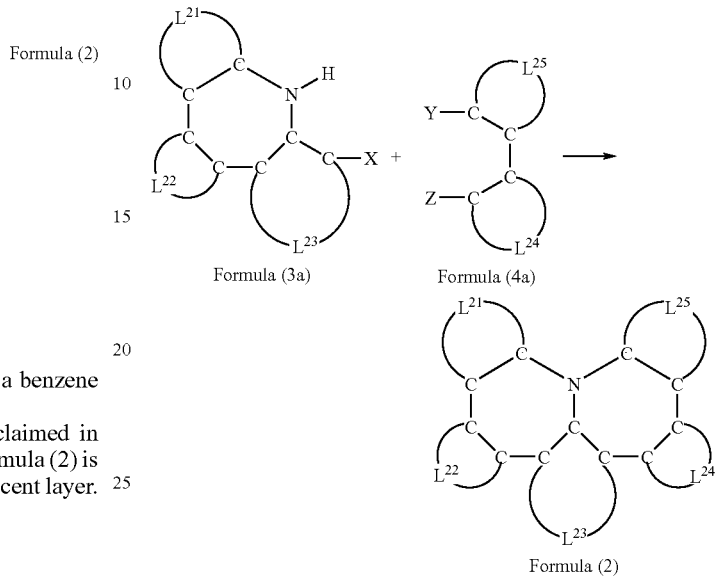

Formula (3a)    Formula (4a)

Formula (2)

wherein $L^{21}$, $L^{22}$, $L^{23}$, $L^{24}$, and $L^{25}$ each form a benzene ring;

X, Y, and Z each independently represent a hydrogen atom or a leaving group, and at least one of Y and Z is the leaving group.

5. The method as claimed in claim 4, wherein the leaving group is selected from the group consisting of a halogen atom, a sulfonyl group, a trifluoromethyl group, and a trifluorobutyl group.

* * * * *